(12) United States Patent
Battlogg

(10) Patent No.: US 10,624,766 B2
(45) Date of Patent: Apr. 21, 2020

(54) PROSTHETIC OR EXOSKELETON COMPONENT, PROSTHESIS OR EXOSKELETON, AND METHOD

(71) Applicant: INVENTUS ENGINEERING GMBH, St. Anton I.M. (AT)

(72) Inventor: Stefan Battlogg, St. Anton I.M. (AT)

(73) Assignee: INVENTUS Engineering GmbH, St. Anton i.M. (AT)

( * ) Notice: Subject to any disclaimer, the term of this patent is extended or adjusted under 35 U.S.C. 154(b) by 128 days.

(21) Appl. No.: 15/575,213

(22) PCT Filed: May 18, 2016

(86) PCT No.: PCT/EP2016/061148
§ 371 (c)(1),
(2) Date: Nov. 17, 2017

(87) PCT Pub. No.: WO2016/184919
PCT Pub. Date: Nov. 24, 2016

(65) Prior Publication Data
US 2018/0147074 A1 May 31, 2018

(30) Foreign Application Priority Data
May 18, 2015 (DE) .................. 10 2015 107 783

(51) Int. Cl.
*A61F 2/68* (2006.01)
*A61F 2/64* (2006.01)
(Continued)

(52) U.S. Cl.
CPC .................. *A61F 2/68* (2013.01); *A61F 2/64* (2013.01); *A61F 2002/5004* (2013.01);
(Continued)

(58) Field of Classification Search
CPC ........ A61F 2/64; A61F 2/68; A61F 2002/704; A61F 2002/705; A61F 2002/7065; A61F 2002/762; A61F 2/605; F16F 9/50–9/537
(Continued)

(56) References Cited

U.S. PATENT DOCUMENTS 5,004,079 A * 4/1991 Ivers .................. F16F 9/46
188/266.5
6,423,098 B1 7/2002 Biedermann
(Continued)

FOREIGN PATENT DOCUMENTS

WO 2006069264 A1 6/2006

*Primary Examiner* — Suba Ganesan
*Assistant Examiner* — Aren Patel
(74) *Attorney, Agent, or Firm* — Laurence A. Greenberg; Werner H. Stemer; Ralph E. Locher

(57) ABSTRACT

A prosthetic or exoskeleton component for a prosthesis or exoskeleton includes a shock-absorbing unit. The shock-absorbing unit contains a damping device that can be controlled by way of a control device. A detection device has a sensor unit for receiving a signal. The detection device is configured to detect uneven ground depending on the acquired signal and to control the damping device in response to the detected uneven ground such that a damping property of the damping device can be adjusted on the basis of a signal of the detection device.

18 Claims, 2 Drawing Sheets

(51) Int. Cl.
*A61F 2/50* (2006.01)
*A61F 2/76* (2006.01)
*A61F 2/70* (2006.01)
*F16F 9/53* (2006.01)

(52) U.S. Cl.
CPC .............. *A61F 2002/5033* (2013.01); *A61F 2002/6881* (2013.01); *A61F 2002/704* (2013.01); *A61F 2002/705* (2013.01); *A61F 2002/762* (2013.01); *A61F 2002/7615* (2013.01); *F16F 9/535* (2013.01)

(58) Field of Classification Search
USPC .................. 623/24; 267/136, 410.14, 410.15
See application file for complete search history.

(56) References Cited

U.S. PATENT DOCUMENTS

| | | | |
|---|---|---|---|
| 6,523,098 B1* | 2/2003 | Anderson | G06F 13/161 |
| | | | 711/156 |
| 7,985,265 B2* | 7/2011 | Moser | A61F 2/6607 |
| | | | 623/50 |
| 8,974,543 B2* | 3/2015 | Balboni | A61F 2/60 |
| | | | 623/43 |
| 9,776,468 B2* | 10/2017 | Teraoka | F16F 9/50 |
| 9,895,240 B2* | 2/2018 | Langlois | A61F 2/60 |
| 2010/0305716 A1 | 12/2010 | Pusch et al. | |
| 2015/0182354 A1* | 7/2015 | Bonnet | A61F 2/64 |
| | | | 623/26 |
| 2017/0205230 A1* | 7/2017 | Send | G01C 3/32 |

\* cited by examiner

PROSTHETIC OR EXOSKELETON COMPONENT, PROSTHESIS OR EXOSKELETON, AND METHOD

BACKGROUND OF THE INVENTION

Field of the Invention

The present invention relates to a prosthesis component or exoskeleton component for a prosthesis or exoskeleton, having at least one shock absorber device, and to a method for operating a prosthesis or an exoskeleton. The shock absorber device comprises at least one damper device that is controllable by way of at least one control device.

Damping has a great influence on the movement properties and therefore constitutes an important feature of a prosthesis or an exoskeleton and, in particular, of arm, leg, hip or foot prostheses. Thus, shock absorbers facilitate an improved gait and allow swift walking, even in rough terrain. Usually, a shock absorber also comprises a spring unit for cushioning occurring shocks and a damping unit for damping the vibration.

In order to be able to exploit the advantages of shocks being absorbed in an ideal fashion, an adjustment of the damping and spring properties is indispensable as a rule. Here, criteria for the adjustment are, for example, the weight of the wearer and their customary movements and the properties of the terrain in which walking should be performed.

To this end, an adjustment of the shock absorber is required as a rule; here, a number of parameters for damping and cushioning must be adjusted and tuned to one another. However, such an adjustment is not always unproblematic especially for beginners or the elderly, who may forget to perform these. In extreme cases, there may even be a deterioration in the wearing properties as a result of a combination of inexpedient adjustments.

Therefore, the prior art has disclosed shock absorbers which, especially for beginners, only provide a few or only the most important adjustment options. In contrast thereto, shock absorbers for advanced users or experts may have a larger number of adjustment options. However, as a rule, a typical wearer of prostheses or exoskeletons is overwhelmed by these.

SUMMARY OF THE INVENTION

It is an object of the present invention to provide a prosthesis or exoskeleton component which simplifies the adaptation of damping properties, in particular during movement.

This object is achieved by a prosthesis or exoskeleton component having the features as claimed, and by a method as claimed. Preferred developments of the invention are the subject matter of the dependent claims. Further advantages and features emerge from the general description and the description of the exemplary embodiments.

A prosthesis or exoskeleton component according to the invention, for a prosthesis or an exoskeleton, comprises at least one shock absorber device with at least one damper device that is controllable by way of at least one control device. Provision is made of at least one identification device with at least one sensor unit, which comprises at least one reception unit for contactless capture of at least one signal and, in particular, a signal that is influenced by at least one area of uneven ground. The identification device is suited and embodied to identify the area of uneven ground depending on the captured signal and to control the, or at least one, damper device or the shock absorber device depending on the identified area of uneven ground such that at least one damping property of the damper device is adjustable by a signal of the identification device.

The prosthesis or exoskeleton component according to the invention has many advantages. A significant advantage is that areas of uneven ground, in the form of obstacles, imperfections, stairs, etc. can be identified and that the damper device is adjusted as a consequence of the identified area of uneven ground. As a result, a very simple and convenient adaptation of the damping properties to the respectively prevalent walking, road or terrain conditions is possible. By way of example, the wearer can change directly from a flat foot path to a difficult path with numerous areas of uneven ground and steps without having to worry about readjusting the damping properties or without a (strong) deterioration of the gait occurring.

A further advantage is that the strength of the damping can be adjusted in a very targeted fashion to a specific area of uneven ground to be reached imminently. Thus, for example, relatively little unevennesses can be damped less strongly than relatively large steps in the terrain. Such an adaptation of the damping properties to the currently prevalent terrain also facilitates an ideal exploitation of the maximum attainable damping of a shock absorber such that the prosthesis is always adapted, even in the case of an extreme movement. As a result of the better exploitation, moreover, the shock absorber can be dimensioned to be smaller, and so weight is also saved.

In particular, the identification device is suited and embodied to characterize, at least in part, the area of uneven ground on the basis of the captured signal. Such a characterization is, for example, the determination of a form or geometry of the area of uneven ground and/or an assignment of the area of uneven ground to a stored category and/or a distance measurement. By way of example, it is also possible to determine the height and/or the angle in relation to the ground and/or the angle of at least one side face of the area of uneven ground.

Within the meaning of the present invention, the phrase area of uneven ground is understood to mean, in particular, at least one disturbance object on or along the path, which can exert a shock on the prosthesis or exoskeleton component in the case of corresponding onward motion such that the damper device becomes active.

In principle, it can be difficult to predict the path since the wearer will, often more or less instinctively, avoid an obstacle if it does not cross the whole width of the path. What may happen in such a case is that an area of uneven ground is identified and the shock absorber device is adjusted or the adjustment is prepared. Subsequently, the obstacle may fail to materialize as a result of circumvention, and so the expected event does not occur because the wearer changed course. However, this does not constitute a problem in preferred configurations as the shock absorber device can be adjusted in less than 30 ms and, in particular, in less than 10 ms, and so a setting which, it turns out, is not needed is not suddenly present. Advantageously, the damper device is equipped with a magnetorheological fluid and a controllable damping valve. An advantage of such a damper device lies in the high speed with which changes can be set.

This means that there is no need to "look" far ahead in order to identify an uneven area of ground. This means that if an area of uneven ground is identified, it also usually becomes relevant. Preferably, an identification of rounding is possible, for the purposes of which, preferably, movements of the body or head are identified and taken into account.

By way of example, the reception unit is embodied as a camera and comprises at least one image sensor. The image sensor preferably is suited to capture an optical projection of the area of uneven ground. It may be possible to capture the optical projection in the range of the visible light and/or in the infrared range and/or in a range with shorter or longer wavelengths. The camera may comprise at least one lens. Provision may be made of at least one filter and/or at least one amplifier device and/or image stabilizor device. A stereo camera for capturing spatial information about the area of uneven ground is also possible.

Preferably, the control device is suited and embodied to modify the damping of the damper device before an identified area of uneven ground is reached and, in particular, set said damping to be stiffer. This is effectuated, in particular, in the case of relatively pronounced areas of uneven ground, the height of which e.g. reaches or exceeds 5 cm or 10 cm. This can ensure that enough range of spring for suitably or ideally dealing with the area of uneven ground is still available when the area of uneven ground is reached. This also applies, in particular, to jumps and other predictable or foreseeable events.

It is also possible for the shock absorber device to comprise at least one controllable spring device. Here, the identification device can be suited and embodied to adjust at least one spring property of the spring device depending on the identified area of uneven ground. By way of example, at least one electrically driven actuator may be provided for adjustment purposes.

The shock absorber device may also comprise a plurality of individual or linked-together damper devices. In particular, at least one damper device of the at least one damper device of the shock absorber device is controllable by the identification device.

In a particularly advantageous configuration, the sensor unit comprises at least one transmission unit. The transmission unit is preferably suited and embodied to emit at least one signal. The reception unit is preferably suited and embodied to receive at least one reflection of the emitted signal, originating at least in part from the area of uneven ground, and to capture said reflection as a signal. The identification device is preferably suited and embodied to identify the area of uneven ground depending on the captured signal. Moreover, the identification device is particularly suited and embodied to control the damper device depending on the identified area of uneven ground such that at least one damping property of the damper device is adjustable by a signal from the identification device. The reflected signal can be processed particularly advantageously by the identification device and it may be used for particularly reliable identification of areas of uneven ground.

The emitted or received signal is, in particular, a transverse wave and/or a longitudinal wave, for example an electromagnetic wave and/or a sound wave. Here, it is possible that the wave has been subjected to appropriate modulations. An emission as a pulse and, in particular, as an ultrashort pulse is also possible. It is possible to provide a pulse phase modulation. The differences between the transmitted and reflected signals are, for example, characteristic for the dimension, the form and/or the material composition of the area of uneven ground. The differences in the transmitted and reflected signals relate to, for example, the amplitude, the frequency, the wavelength, the phase and/or the polarization. It is also possible to ascertain interferences between an emitted signal and a received signal. By way of example, the sensor unit is embodied as an interferometer or it may comprise the latter. Preferably, signals in the range of shorter wavelengths are used to this end, for example visible light.

Preferably, the transmission unit and the reception unit are integrated in at least one common sensor. It is also possible that the transmission unit and the reception unit are embodied separately. The transfer between the sensor unit and the identification device may be effectuated wirelessly in this case. However, provision may also be made of at least one corresponding connection line.

In particular, the damper device comprises at least one first damping chamber and at least one second damping chamber. The damping chambers are, in particular, coupled to one another by way of at least one controllable damping valve. The adjustable damping property is, in particular, at least one measure of the damping. By way of example, the damping property is a stiff or soft damping.

In a particularly preferred development, at least one controllable field generating device is assigned to the damping valve. In particular, the field generating device is suited and embodied to be controlled by the identification device. By way of example, an electrical coil may be provided to this end. In particular, the field generating device is suited and embodied to generate and/or control a field strength in at least one damping duct of the damping valve. Here, a field-sensitive rheological medium is preferably provided in the damping duct.

Preferably, the damper device is provided with at least one magnetorheological fluid and preferably said damper device has at least one adjustable magnetorheological damping valve. At least one mechanically actuable damping valve is also possible. Particularly preferably, a magnetorheological medium and, in particular, a magnetorheological fluid is used as rheological medium. Here, in particular, the resultant viscosity of the fluid is influenced via the intensity and strength of the magnetic field built up by the field generating device.

In a further particularly preferred development, the identification device is suited and embodied to control the damper device depending on areas of uneven ground which lie in a near region. Preferably, only areas of uneven ground in the near region are taken into account. In particular, the near region is defined by at least one specification stored in the identification device, for example by a distance, length and/or width, and/or by an angle. A dynamically adaptable near region is also possible. The near region can also be adjustable by a prescription of the user.

By way of example, the near region may be 1 m or 2 m or 3 m, or else 5 m or else more. It is also possible for the near region to extend over 10 m or 15 m or even 20 m or more. However, particularly preferably, the near region may also be less than 1 m and, for example, be 70 cm or 50 cm or 20 cm or else 10 cm or less. Preferably, the near region extends forward from a region lying at the front end of the prosthesis or exoskeleton in the direction of walking. By way of example, the near region starts in front of the tips of the toes. Particularly preferably, the near region is shorter than 5 m and, in particular, shorter than 2 m.

Taking into account areas of uneven ground in a near region offers significant advantages because numerous and very quick changes in direction are often undertaken when walking and, in particular, when walking in terrain. Consequently, a long-term anticipatory identification would not be expedient and tends to be disadvantageous since areas of uneven ground which play no role may be taken into account. What is shown in this case is that, in particular, a transfer of obstacle identification systems known from the automotive sector does not lead to a solution to the aforementioned problem. In the automotive sector, it is necessary to identify obstacles which lie as far ahead as possible and which represent a danger for the onward travel on the selected route. Following on from this, a different characteristic of the damper is subsequently selected. The dampers or pneumatic suspensions used in the prior art are "slow" in relation to the damper according to the invention (prior art: approximately 100 ms elapse between the identification and the attainment of the ideal adjustment position of the damper for technological reasons; this is <10 ms in the article according to the invention). As a result thereof, the prior art is not even able to effectuate many actions of the article according to the invention or entirely new options open up as a result of the fast reaction time of the article according to the invention in an inventive combination with selected image processing and sensors.

By contrast, in the field of prosthetics, it is desired, as a rule, to advance to the area of uneven ground and to overcome the latter. Consequently, the invention presented here should not promote a circumvention of obstacles but, precisely, a traversal over areas of uneven ground by way of a very quick adaptation of damping properties.

Particularly preferably, the identification device is also suited and embodied to predetermine the near region depending on the walking speed of the wearer of the prosthesis or exoskeleton. Preferably, the near region extends, in particular, over at most the distance which can be covered in one second when walking. Setting the near region in this manner depending on the walking speed offers the advantage that, essentially, those areas of uneven ground which are also relevant to the damper load are taken into account. By way of example, those areas of uneven ground which are situated at a distance of approximately one walking second from the tips of the toes will also be traversed with a very high probability. It is also possible for the near region to extend at most over the distance which the prosthesis or the exoskeleton traverses in less than one second and, for example, in half a second or, particularly preferably, in 0.2 seconds or, preferably, 0.1 seconds or less on account of the walking speed, which, in turn, is very advantageous in the case of fast walking in terrain. The prosthesis or exoskeleton component according to the invention not only identifies situations (e.g. a root) by means of the near field identification systems but also quantifies the latter (distance to the root, root height, root length, one or more roots . . . ) and appropriately adjusts the prosthesis or exoskeleton component as late as possible or in a timely fashion or regulates the latter to the best possible extent in real time while overcoming the obstacle on account of the identification information in order, straight thereafter, to set different damping, once again in real time. The changeover that is as late as possible before the event and the restoration which as quick as possible after (e.g. <5 ms) said event has great importance in terms of safety aspects. A damper which is set to "very soft or resilient" too early or for too long on account of e.g. a root greatly increases the body movements and reduces the stability; unstable states may arise and falls as a result thereof are possible.

Identifying the situations without near field identification systems, for example with multi-axis acceleration sensors, is a great problem in the prior art and requires many sensors for identifying and assigning situations. In addition to costs, this also increases the power requirement. Moreover, an enormous amount of development outlay is required in order to correctly analyze all possibly occurring states and sensor signals. In actual fact, current systems without near field identification can, in a certain way, be compared to visually impaired persons, making everyday life more difficult. A blind person's cane, a guide dog and, in particular, the "eyesight" thus have an uncontested and verifiably great advantage.

By way of example, if the prosthesis does not correctly identify a situation (downward steps or stairs) and the prosthesis wearer then falls over because the damping is set to be too soft or set incorrectly, this leads, in addition to possibly serious injuries, to the loss of faith in the prosthesis. This significantly impairs the wearing behavior.

The best non-near-field-identification sensors in/at the prosthesis cannot identify e.g. a branch or a rope, etc., traversing the forest path. The quickly running prosthesis wearer may stumble here because the damper does not leave the leg bent longer than previously when stepping/jumping thereover, as is done instinctively by the human when the obstacle is seen and crossed by jumping as evasion is no longer possible. If the surroundings identification system sees and identifies the obstacle, the ideal angle of the prosthesis can be calculated and actuated accordingly. Then, the overall package is dependent on the situation and anticipatory; the prosthesis wearer suffers no injury.

By way of example, steps or stairs or ramps place high requirements on the dampers since the forces in this case are much greater than, for example, when walking in the flat: walking in the flat requires a damping force of approximately 1500 N. By contrast, stairs or a downward ramp require up to 6000 N. Hence, the damper must be set to be much stiffer (up to a factor of 3) already at (or prior to) the first downward step; otherwise, the damper is displaced too quickly on account of the soft setting and the high introduced forces and too much path is given away until the ideal damping is identified and set (prior art: approximately 60 ms valve adjustment time). Consequently, what may even occur now is that, before the damper is correctly set (adjusted), the latter has already traversed the entire displacement path and has arrived at the end stop. Consequently, the prosthesis wearer sinks much too quickly in order thereafter to arrive at the stop abruptly, possibly leading to a fall or strong loads. This can be identified and avoided by a timely identification of this situation by means of the sensors described herein.

By way of example, another example is given by the situation where a jump is identified (e.g. two steps are skipped . . . ) and the approximate landing time/point is calculated. Then, the overall system controls the damper accordingly in the best possible way=stiff damping, and so the prosthesis wearer does not bend the knees too strongly and, possibly, as a result thereof does not end up in an advanced position of the upper body with a subsequent fall.

However, it is also possible for the near region to extend over the distance which the prosthesis or exoskeleton covers in more than one second and, for example, 1.5 seconds or 2 seconds or 3 seconds on the basis of the walking speed. The prosthesis or exoskeleton component may comprise suitable sensors for determining the walking speed. It is also possible to query a speedometer and/or navigation system of the prosthesis or exoskeleton wearer.

The time by means of which the extent of the near region is defined can be set depending on a width of the near region. Here, in particular, the width of the near region extends transversely to the walking direction. The width of the near region may also be set by a capturing angle of the sensor unit. By way of example, the capturing angle is determined by virtue of the angle at which the signal is emitted and/or the angle at which the reception unit receives a reflected signal. Such a configuration is advantageous since the width of the near region has an influence on how quickly an identified area of uneven ground can be circumvented by an evasive maneuver and consequently becomes irrelevant to the damper control.

Preferably, the identification device is suited and embodied to adjust the damping property of the damper device in less than 30 milliseconds as a consequence of an identified area of uneven ground in the near region. Here, this period of time should be understood to mean, in particular, the time that is required for the corresponding damper adjustment after identifying an area of uneven ground. Preferably, the evaluation of the sensor signals and the identification of the area of uneven ground is also effectuated in such a time period and, particularly preferably, in a significantly shorter time period.

In particular, the damper device is also suited and embodied to be adjusted by the identification device within the aforementioned time. Such a short adjustment time is advantageous in that it is possible to implement correspondingly short near regions. This increases the probability that the identified areas of uneven ground also really become relevant. A further advantage is that a complete adaptation of the damping property still is possible in the case of a sudden maneuver where new identification of areas of uneven ground become necessary as a consequence thereof.

Particularly preferably, the quick adjustment of the damping property is effectuated by means of the damper valve and the assigned field generating device. In particular, the damping property of the damper device is adjusted in less than 20 milliseconds or less than 10 milliseconds and particularly preferably in less than 5 milliseconds. The adjustment may also be effectuated in less than 3 milliseconds and, in particular, in less than 2 milliseconds. However, an adjustment which requires more than 30 milliseconds and, for example, 50 milliseconds is also possible.

In particular, the identification device is suited and embodied to ascertain the height of the area of uneven ground above the ground and take this into account for controlling the damper device. Preferably, the identification device is suited and embodied to ascertain the angle of at least one region of the area of uneven ground with respect to the ground and take this into account for controlling the damper device. By way of example, the damping may be set to be softer with increasing steepness and/or height of the area of uneven ground.

By way of example, the control is effectuated in this case within the meaning of a characteristic field control, and so corresponding values of height and/or angle are assigned to stored values for the damper stiffness. A threshold-dependent control is also possible, and so an assigned damper stiffness is set when thresholds in respect of height and/or angle are overshot and/or undershot. It is also possible for the control to be embodied as an adaptive control. To this end, the control may comprise, for example, an adaptive algorithm and/or a fuzzy logic and/or an algorithm based on the principle of a neural network or the like.

In an advantageous configuration, the identification device is suited and embodied to ascertain a distance from the area of uneven ground. Here, it may be the case that the signals captured by the sensor unit are characteristic for a distance between the area of uneven ground and the sensor unit. By way of example, a correction factor, by means of which a distance between the leg and the area of uneven ground is calculable from the distance between the sensor unit and area of uneven ground, may be provided.

On the basis of the information about the distance between the tips of the toes and the area of uneven ground, it is possible to calculate the time when the foot comes into contact with the area of uneven ground. Thus, for example by taking account of the walking speed, the damper adjustment can be undertaken exactly when the adaptation to the area of uneven ground is necessary—to be precise, even exactly at the moment when it is required. In combination with a configuration described above, in which a field generating device is used for adjusting the dampers, very fast and short-term reactions are possible in such a case, and so a reaction to areas of uneven ground lying directly in front of the foot still can also be effectuated with an ideal damper setting.

In particular, a range of spring can be saved ahead of the area of uneven ground in the case of an anticipatory identification of an area of uneven ground, such as an object lying on the road or foot path, a thick root or the like, in order still to reliably have enough range of spring available for ideal damping for the purposes of overcoming the area of uneven ground (root, stone, etc.). Without anticipatory identification, it could be necessary to set the damping much stiffer than actually desired when traversing the area of uneven ground if the available range of spring has already been used up or there is danger of a breakdown.

In all cases, it is also possible that the distance of an area of uneven ground can already be deduced from the identification thereof per se. Then, an additional determination of distance is preferably not necessary. By way of example, this is the case if the capture range of the sensor unit is focused accordingly such that only areas of uneven ground lying at a certain distance are registered in any case. Then, it is possible to ascertain the time at which the prosthesis comes into contact with the area of uneven ground, for example directly after identifying the area of uneven ground and by taking into account the walking speed and a distance factor.

The identification device is preferably also suited and embodied to take account of at least one preset limit for maximum damping when controlling the damper device. The control can also take account of a limit for minimum damping. Here, the limit can be set by the user. Limits in the form of factory presets are also possible. However, it is also possible that the limit is set automatically after at least one user input. By way of example, the driver can enter their weight by means of a user interface and a limit for minimum damping and maximum damping is subsequently set. Optionally, the weight of the wearer is ascertained by sensors.

Such configurations are advantageous in that the adjustment of the damper device by the identification device does not lead to settings that are problematic or unwanted by the user. Thus, provision can also be made for the control to be briefly deactivated depending on identified areas of uneven ground in the case of certain situations, in which a high damper load is sensed. To this end, a damper controller, for example, can be provided and embodied, the latter comprising damper sensors and carrying out the control commands of the identification device according to a certain priority.

In an advantageous development, the prosthesis or exoskeleton component for a shock absorber device is provided with at least one first damper device and at least one second damper device. Here, the first damper device is preferably assigned to a hip damper and the second damper device is preferably assigned to a knee damper. In particular, the identification device can be suited and embodied to set the second damper device with time delay in relation to the first damper device. The identification device is preferably embodied to set the damper devices independently of one another.

Such a time-delayed actuation may be advantageous in that the damper device of the knee is also prepared in ideal fashion and can be adapted to the area of uneven ground at the ideal time. Here, it is preferable for the identification device to be suited and embodied to adapt the time delay depending on the walking speed of the prosthesis or exoskeleton wearer. In particular, the kinematics between hip and knee are also taken into account. It is possible that the damper device is assigned to at least one detector device or a sensor module for capturing a damper load. By way of example, a detector device (damper sensor) can be provided, said detector device capturing the travel and/or the speed of two components of the damper device that are movable in relation to one another. In particular, the detector device can be used to capture how far and/or how quickly the damper contracts in the case of an impact and/or expands again after an impact. Here, the detector device can be part of the prosthesis or of the exoskeleton which is assigned to the prosthesis or exoskeleton component. However, it is also possible that the detector device is comprised by the prosthesis or exoskeleton component.

By way of example, some damper controllers are already equipped at the factory with appropriate sensors for identifying the load, in particular in order to be able to undertake an independent adaptation. Preferably, the identification device is suited and embodied to read such sensor data and take these into account when setting the damper property.

Preferably, the identification device is suited and embodied to register the damper load after an impact on a previously identified area of uneven ground. This allows conclusions to be drawn as to whether or not the adjustment of the damper property, performed as a reaction to the identified area of uneven ground, was productive. Preferably, the identification device can compare the registered damper load with values for a damper load stored in at least one storage device.

Particularly preferably, the identification device is embodied in such a way that the controller can be adapted to the damper device if the registered damper load deviates from at least one predetermined measure for the damper load. Here, the adaptation of the controller is preferably undertaken in such a way that a better damper load within the range of the predetermined measure is achievable in future areas of uneven ground. Preferably, the identification device is equipped with at least one adaptive algorithm.

In particular, the identification device is embodied in such a way that it can autonomously check the set damper settings and that it adapts future control commands to the damper device by at least one correction factor in the case of an occurrence of inexpedient damper loads such that the damper load in future lies in an ideal range again.

It is also possible for provision to be made for at least one sensor module for capturing a spring load of at least one spring device. Here, the identification device is, in particular, suited and embodied to read the sensor module and adapt the control of the spring device, as was also described above for the damper load.

It is preferable for the identification device to have at least one storage device for storing the identified areas of uneven ground. The storage device preferably has a functional connection to at least one interface such that a readout of the recorded areas of uneven ground is possible, for example by a user. It is also possible that the identification device can independently read the storage device, for example for an automatic correction. It is also possible that the storage device is embodied to record the damper load and/or the set damper settings. Capturing such data facilitates particularly simple monitoring of the settings, set by the user, on the shock absorber device.

It is particularly preferred for the sensor unit to be arranged at at least one component of the prosthesis or of the exoskeleton. This is advantageous in that the sensor unit is substantially always aligned in the direction of walking. It is also possible to arrange the sensor unit at a different body part of the wearer. Here, it is possible for the transmission unit and the reception unit to be arranged at a distance from one another and/or on separate components. Preferably, the sensor unit is received in a pivotable manner in at least one holder device. Here, the holder device, in particular, is embodied with a fastening element which is arranged on a component of the prosthesis or exoskeleton. Moreover, the holder device comprises at least one second fastening element which is provided for connection with the sensor unit. Preferably, an assembly or disassembly of the sensor unit on the holder device without tools is provided. In particular, the holder device can also be fastened on, or disassembled from, the prosthesis or exoskeleton without tools.

Particularly preferably, the sensor unit is assembled in a pivotable manner on the prosthesis or the exoskeleton by means of the holder device. In particular, the pivotability is embodied in such a way that the transmission angle and/or the reception angle of the sensor unit with respect to the ground is adjustable. By way of example, scaling and/or a lattice can be provided on the holder device such that the user is provided with an aid when aligning the sensor unit. Such pivoting of the sensor unit is advantageous in that the capture region for identifying areas of uneven ground can be adapted quickly and with little outlay.

In particular, there is an adaptation of the identification device in respect of the damper actuation according to identified areas of uneven ground after such pivoting of the sensor unit. Such an adaptation is particularly easy if the identification device has an adaptive embodiment. Then, for example, the identification device is able to independently ascertain the distance between the capture region of the sensor unit and the user, and thereafter adjust the damper actuation, after passing over one or more areas of uneven ground taking into account the walking speed.

However, it is also possible that a pivoting of the sensor unit and/or any other change of the capture region of the sensor unit requires a manual adjustment at the identification device. By way of example, a light source which transmits an illuminated dot into the capture region may be arranged at the sensor unit. Then, the user is able to measure the distance between the illuminated dot and the foot and enter the measured distance within the meaning of a correction factor into the identification device by way of an input device or any other interface.

In particular, the sensor unit is arranged at at least one holder device such that a spaced apart arrangement in relation to at least one component of the prosthesis or of the exoskeleton emerges. By way of example, a clamp may be provided. In a further preferred embodiment, the sensor unit is embodied as an ultrasound sensor or comprises at least one such device. Such ultrasound sensors are cost-effective and have very compact dimensions. Moreover, a configuration of the identification system with a very low weight is possible using such sensors; this is an important feature, particularly in the cycling sport sector.

Moreover, ultrasound sensors allow a reliable identification of areas of uneven ground and, in particular, the height, angle and/or distance thereof. It is also possible for the sensor unit to comprise two or three or more ultrasound sensors. Thus, for example, provision can be made of a 2, 4 and/or 6 channel and/or more channel system.

The sensor unit may also comprise at least one infrared sensor or be embodied as such a sensor. Infrared sensors also offer a cost-effective and reliable sensor system for identifying areas of uneven ground and the geometry or distance thereof. Here, provision may also be made of two or three or more infrared sensors.

Use can also be made of cost-effective depth sensors, as used in e.g. the Microsoft Kinect.

The sensor unit may also be a head mounted display (HMD), a near-to-eye optical system (such as e.g. Google glass) or a development of these technologies, or it may be complemented thereby. Using this, it is possible to obtain, inter alia, additional information as well, because the following is identified: the direction and where to or on what the gaze is directed (rotational angle of the head, inclination of the head, focus; movement speed . . . ). Here, the wearer of the HMD automatically looks on the objects relevant to the situation and thereby makes the preselection. This simplifies the situation analysis and increases the predictive accuracy of the near field identification. It is also possible to superimpose information for the wearer (e.g. reduce speed) in order thus to obtain an improved result in combination with the adaptation of the dampers derived from the sensor signal.

It is also possible that the sensor unit is embodied as at least one radar system or at least comprises such a system. By way of example, the sensor unit may be embodied as a so-called ultra wide band radar sensor. Here, the sensor unit is embodied to emit at least one ultrashort pulse and to receive again and evaluate the corresponding reflections. By way of example, it is possible to use a change in phase, frequency, wavelength and/or time-of-flight to identify the area of uneven ground.

A prosthesis or exoskeleton component may also comprise further components and parts such that a prosthesis or exoskeleton component may also form a complete prosthesis or a complete exoskeleton.

The method according to the invention is suited to operate a prosthesis or exoskeleton component which is provided for a prosthesis or exoskeleton. The prosthesis or the exoskeleton comprises at least one shock absorber device with at least one damper device. The damper device is controllable by way of at least one control device. Here, at least one signal and, in particular, a signal influenced or originating from at least one area of uneven ground is captured contactlessly by means of an identification device. The area of uneven ground is identified on the basis of the signal captured contactlessly. The damper device is controlled depending on the identified area of uneven ground. Here, at least one damping property of the damper device is adjusted.

The method according to the invention is advantageous in that areas of uneven ground are identified automatically and the shock absorbers are subsequently adjusted in such a way that the areas of uneven ground are passed with damping properties that are as ideal as possible.

Preferably, at least one signal is emitted by means of the identification device and at least one reflection of the emitted signal, originating from the area of uneven ground, is received and captured as a signal.

After identifying the area of uneven ground, the damper device is preferably adjusted to be stiffer until the area of uneven ground is reached. In particular, the anticipatory identification of an area of uneven ground allows sufficient range of spring to be saved for the area of uneven ground, and so an ideal damping of the area of uneven ground can be effectuated.

Particularly preferably, a prosthesis or exoskeleton component as described in one of the preceding claims finds use in the method according to the invention. It is also particularly preferred for the damper device to be adjusted on the basis of a controllable field generating device and by means of a field-sensitive rheological medium.

Preferably, not only dynamic obstacles, extensive paths, terrain forms, etc. but also static obstacles or situations are captured and considered accordingly from a control point of view in the method according to the invention:

During a stay at a reception or in a bar (long calm standing), thus can be treated differently from a control point of view (sampling rate, current requirement, first setting . . . ) than the wait in front of an elevator or in the case of a red traffic light (brief standing with subsequent step/sidewalk edge and occasional fast running off . . . ).

No holding force is required if the prosthesis wearer is standing at the bar with a straight leg. In this case, the actuator, preferably an actuator with a magnetorheological liquid, can reduce the query time (clock of the electronics) in order to save power. This then goes as far as a "sleep mode" which saves much power. If the situation is not identified and the MRF actuator is switched to be currentless, this may be problematic or dangerous should the prosthesis wearer move very suddenly and the valve be fully open (because of no current) and the prosthesis wearer therefore bends over. In order to counteract this here, short internal electronic query times must be set despite the calm standing=no power requirement for the MRF valve; this increases the power requirement. This is also the case because, for example, standing at a bar may be a process extending for hours on end. The reduction in the power requirement is very important as this saves weight and installation space, and increases the use duration.

By means of at least one sensor such as e.g. a head up display with image and/or speech recognition (advanced data goggles), it is possible to identify whether or not the prosthesis wearer intends to move away. It will initially identify the surroundings accordingly (turning of the head; possibly by way of speech recognition and the analysis of the spoken word such as "bye"; "I am leaving now"; "I would like to settle the bill, please") and then run off. In combination with the identification of the surroundings and the situation analysis, it is possible to evaluate the situation to a better extent and sometimes it can only be evaluated at all.

According to the prior art, an arm/finger/limb stump is required for controlling an e.g. prosthesis or else an active prosthesis. For many people, this does not work because, for example, they are seriously disabled (e.g. paralyzed from the cervical spine downward). Sensors and speech recognition and image recognition assist walking aids and other aids. As a result, they can be controlled in an improved manner. Here, the sensors can help by virtue of situations being identified and, as result thereof, actions being carried out, as described above. These are advantageous in combination with speech commands.

At the start of the development, there is an autonomous system (e.g. prostheses), the behavior of which is improved by "anticipation". Successively, with increasing refinement of the sensors, etc., the "anticipation" assumes more functions.

The prostheses or exoskeleton components according to the invention can also be used by prostheses wearers when skiing, surfing or other applications.

The "anticipation" need not necessarily be optical; instead, it can also be acoustic. By way of an acoustic sensor (microphone; frequency, loudspeaker, voice recognition . . . ), it is possible to use the surface during fast walking (tar=quiet; gravel=loud; sounds of wind=quick . . . ) and, resulting therefrom, it is possible to modify the damper setting. This also applies to acoustic advice and warnings by other persons and automatic advice and warnings or information (lift doors closing; attention, escalator . . . ).

Typically, prostheses or exoskeleton users must also, at least occasionally, carry loads such as a rucksack or lift and carry objects, receive a package, etc. The sensor unit or the image recognition unit including evaluation already identifies the situation preferably in an anticipatory manner here or estimates e.g. the load, the load distance and the angle. It is also possible to take account of extended arms and angled arms, etc. The control device adapts the damper accordingly; by way of example, the damper is or dampers are set to be stiffer and/or the characteristics are adapted. As a result, it is possible, for example, to avoid too quick a displacement to the end stop or other inexpedient situations.

Further advantages and features of the present invention emerge from the description of the exemplary embodiments, which are explained below with reference to the attached figures.

DESCRIPTION OF THE INVENTION

With reference to the attached figures, an exemplary embodiment of a prosthesis or exoskeleton 200 that is equipped with a prosthesis or exoskeleton component 401 and with shock absorbers 100 is explained below.

Figure 1:
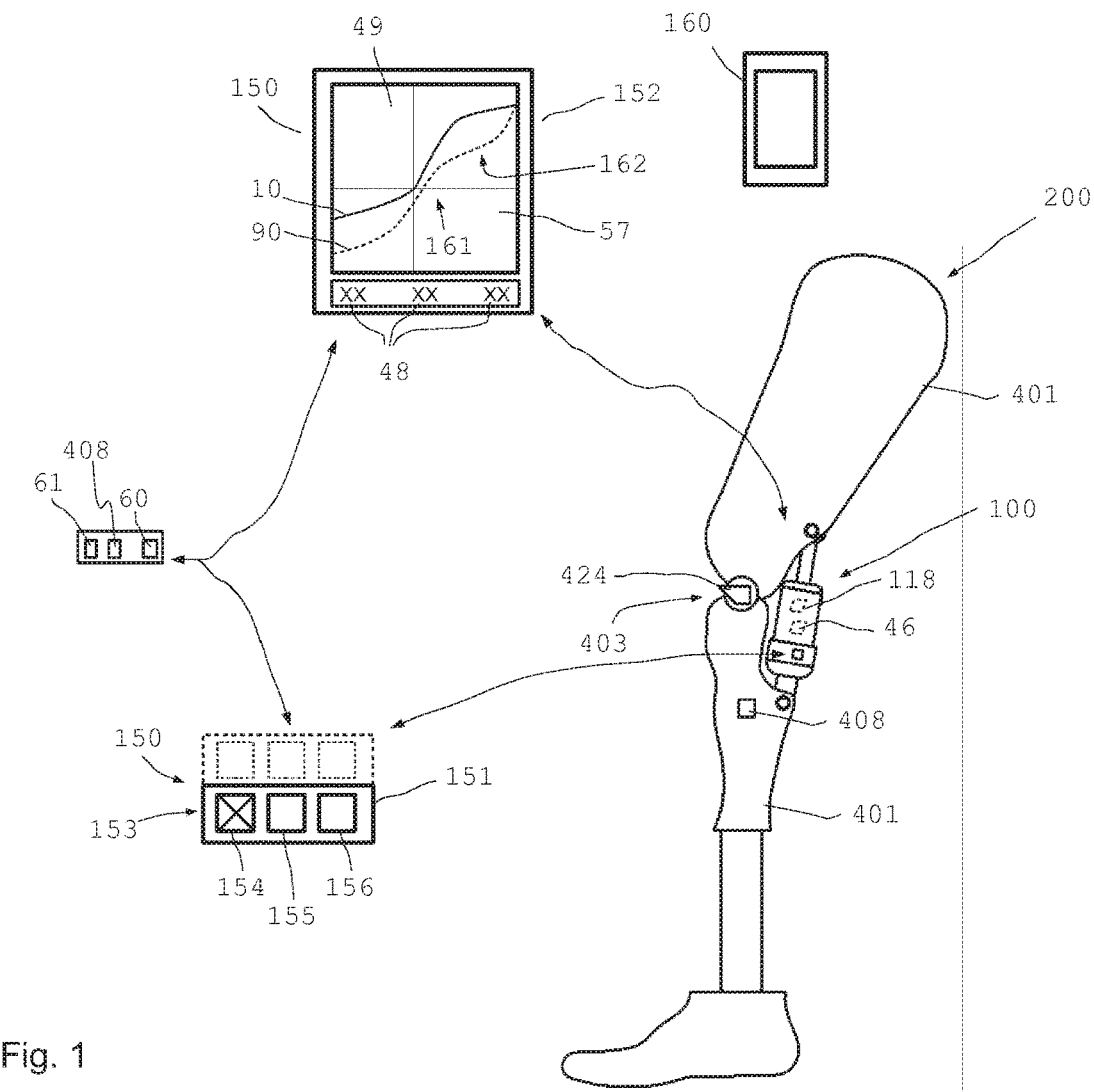
FIG. 1 shows a schematic view of a prosthesis equipped with a prosthesis or exoskeleton component according to the invention.

FIG. 1 shows a schematic illustration of a prosthesis 200. The prosthesis comprises a shock absorber 100 which comprises at least one damper device. Here, a central control device 60 is provided in a container together with a battery unit 61.

Additionally, each shock absorber 100 in this case has at least one control device 46 on an electronics unit that is provided in a replaceable manner. The electronics units may each have separate battery units. However, a power supply through the central battery unit 61 is preferred.

The damper controller and the central control device 60 are operated via operating devices 150. Two operating devices 150 are provided, namely an actuating device 151 and an adjustment device 152. The actuating device 151 has mechanical input units 153. The adjustment device 152 may be embodied as a computer. However, it is also possible that a smartphone 160, a smart watch (smart device) or a tablet or the like is used as an adjustment device 152 and, for example, stored in the pocket or in the backpack of the user when no adjustment of the settings is undertaken.

It is also possible that two shock absorbers are controlled synchronously by way of an actuating device 151.

The display 49 is embodied, in particular, as a graphical user interface or as a touchscreen 57 such that the user may, for example, touch an illustrated damper characteristic 10 with the fingers and modify it by dragging. As a result, the illustrated damper characteristic 90, which is used immediately for the control, can be produced from the damper characteristic 10, illustrated using solid lines, by contacting one or more points. The modification of the damper characteristics 10, 90 is also during operation, for example when walking. Here, it is not only the damping that is modified but it is also possible to simultaneously, or else exclusively, modify the suspension.

The adjustment device 152 may also serve as a display computer and display information about the current speed and about the average speed and/or the daily, tour, lap and overall kilometers. It is also possible to display the current position, the current time, the current elevation, the traversed path and the path profile, and also a possible range under current damping conditions.

The prosthesis 200 shown here is equipped with a prosthesis or exoskeleton component 401 according to the invention. The shown prosthesis 200 with the prosthesis or exoskeleton component 401 can be controlled according to the method according to the invention.

In the configuration shown here, the prosthesis or exoskeleton component 401 comprises an identification device 408 which is integrated into the central control device 60. The identification device 408, however, may also have a separate embodiment and may be housed at any suitable location on the prosthesis wearer 200. Here, the prosthesis or exoskeleton component 401 moreover comprises a sensor unit 403 which comprises an ultrasound sensor 424 attached to the prosthesis wearer. Here, the sensor unit 403 is connected to the identification device 408 by way of a line (not shown). Alternatively, a wireless communication may also be provided between the sensor unit 403 and the identification device 408.

During the operation, the sensor unit 403 emits an ultrasound signal and receives the reflection thereof. The identification device 408 evaluates the received signal and thus recognizes whether the source of the reflection is an area of uneven ground in the terrain. Here, the reflected signal is also, in particular, evaluated by the identification device 408 in such a way that a characterization of the area of uneven ground is possible. As a consequence of an identified or characterized area of uneven ground, the identification device 408 supplies a corresponding control signal to the central control device 60.

Thereupon, the central control device 60 influences an embodied first damper device. The adjustment of the damper device 100 by the control device 60 is explained in more detail with reference to FIG. 3.

The walking speed may also be determined by way of a GPS signal.

Figure 2:
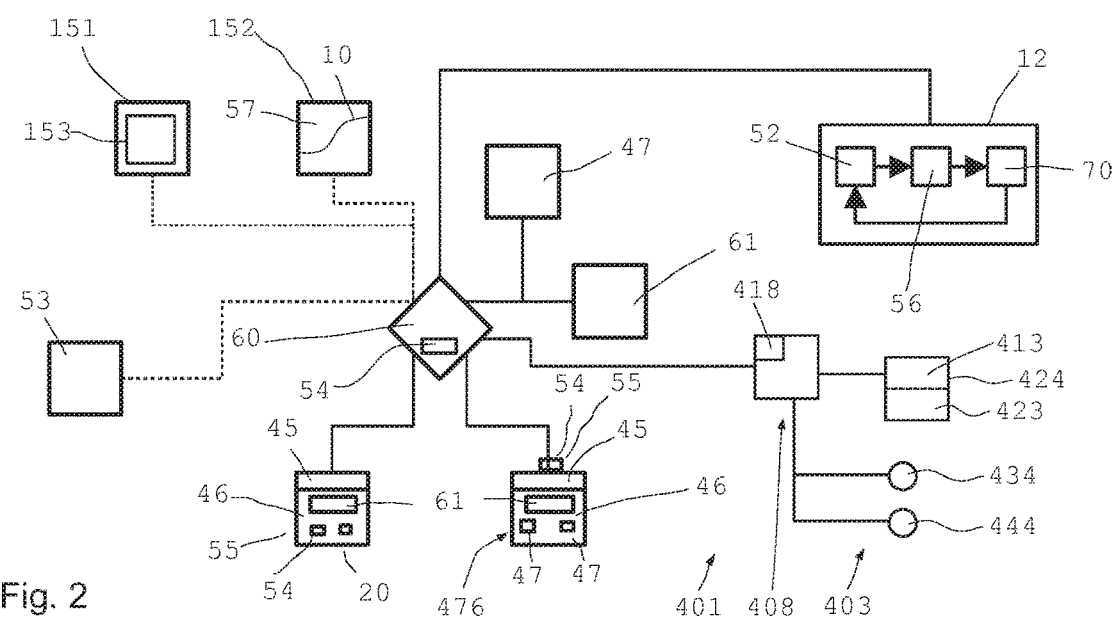
FIG. 2 shows a schematic view of the control structure of the prosthesis or of the exoskeleton according to FIG. 1.

FIG. 2 shows a schematic illustration of the damper controller 300 and the communication links of some of the involved components. The central control device 60 may be connected to the individual components in a wired or wireless manner. By way of example, the control device 60 can be connected to the other components via WLAN, Bluetooth, ANT+, GPRS, UMTS, LTE or any other transfer standards. Optionally, the control device 60 may be connected wirelessly to the Internet 53 via the link illustrated by dots.

The control device 60 is connected to the battery unit 61. Furthermore, the control device 60 can be connected to a detector device 20 or to a plurality of sensors. The operating devices 150, namely the actuating device 151 and the adjustment device 152, are coupled, at least intermittently, to the control device 60 in a wired or wireless manner. The actuating device 151 is preferably coupled to the control device in a wired manner; however, it may also be linked wirelessly and may comprise a separate battery such as a button cell or the like.

The control device 60 is connected via cables, network interfaces 54 or radio network interfaces 55 to control devices 46 of the shock absorbers 100 at the prosthesis. The control device 46, possibly provided at each shock absorber 100, ensures the local control and may in each case have a battery or else may be connected to the central battery unit 61. It is preferable for the control of both shock absorbers to be effectuated by way of the control device 60.

Preferably, at least one detector device 20 is assigned to each shock absorber 100 in order to capture relative movements between the components 101 and 102 and in order, in particular, to determine a relative position of the components 101 and 102 relative to one another. The detector device 20 may be embodied as a position sensor or else comprise the latter. On the basis of the damper characteristic 10 of the shock absorber 100 stored in the storage device 45, the associated damping force and a suitable spring force is adjusted after ascertaining a characteristic for the relative speed. A suitable spring force may be ascertained by way of the current weight of the user.

In FIG. 2, the control circuit 12, which is saved in the storage device 45 and stored or programmed in the control device 60, is illustrated schematically. The control circuit 12 is carried out periodically during operation and, in particular, carried out periodically in a continuous manner. In step 52, a current relative movement or relative speed of the first component 101 in relation to the second component 102 is captured with the detector device 20. A characteristic which is representative for the current relative speed is derived in step 52 from the values of the detector device 20 or of the sensors.

In the next step 56, the associated damping force to be set is then subsequently derived from the current or ascertained characteristic value, taking into account the predetermined or selected damper characteristic. From this, a measure for the field strength or current to be set at the current time is derived; by means of this, it is possible to at least approximately obtain the damping force to be set. The measure may be the field strength itself, or else e.g. specify the current at which the damping force to be set is obtained at least approximately.

In a subsequent step 70, the latest field strength to be set is produced or the corresponding current is applied to the electric coil device 11 as a field generating device such that, within a single cycle or a time period of the control circuit 12, the damping force which is provided in the case of the selected or predetermined damper characteristic in relation to the current relative speed of the first component in relation to the second component is produced. Subsequently, the next cycle starts and step 52 is carried out anew.

The central control device 60 shown here moreover has a functional connection to the prosthesis or exoskeleton component 401 according to the invention. The prosthesis or exoskeleton component 401 consists of the identification device 408 and an ultrasound sensor 424. Here, the ultrasound sensor 424 can emit an ultrasound signal and can also receive this signal again. The sensor 424 consequently unifies a transmission unit 413 and a reception unit 423 in one component. As a result, a particularly inconspicuous and space-saving housing is possible. This is advantageous in the case of sports prostheses in particular, in which increased value is placed on a low weight and good aerodynamic properties. Moreover, the external appearance of the prosthesis 200 is not impaired either.

Alternatively, the identification device 408 may also be connected to an infrared sensor 434. Provision can also be made of a radar sensor 444. Here, the identification device 408 also has an integrated storage device 418. Hence, storing the identified areas of uneven ground (or the data thereof) and the subsequently undertaken damper adjustments is possible. Later, this can be retrieved, e.g. by a user, via an appropriate interface such as e.g. a smartphone 160. Moreover, the identification device 408 in this case resorts to data of a sensor module 476 which is embodied as a detector device 20. Here, the identification device 408 takes account of the captured values of the detector device 20 in order to be able to monitor the damper load.

Figure 2A:
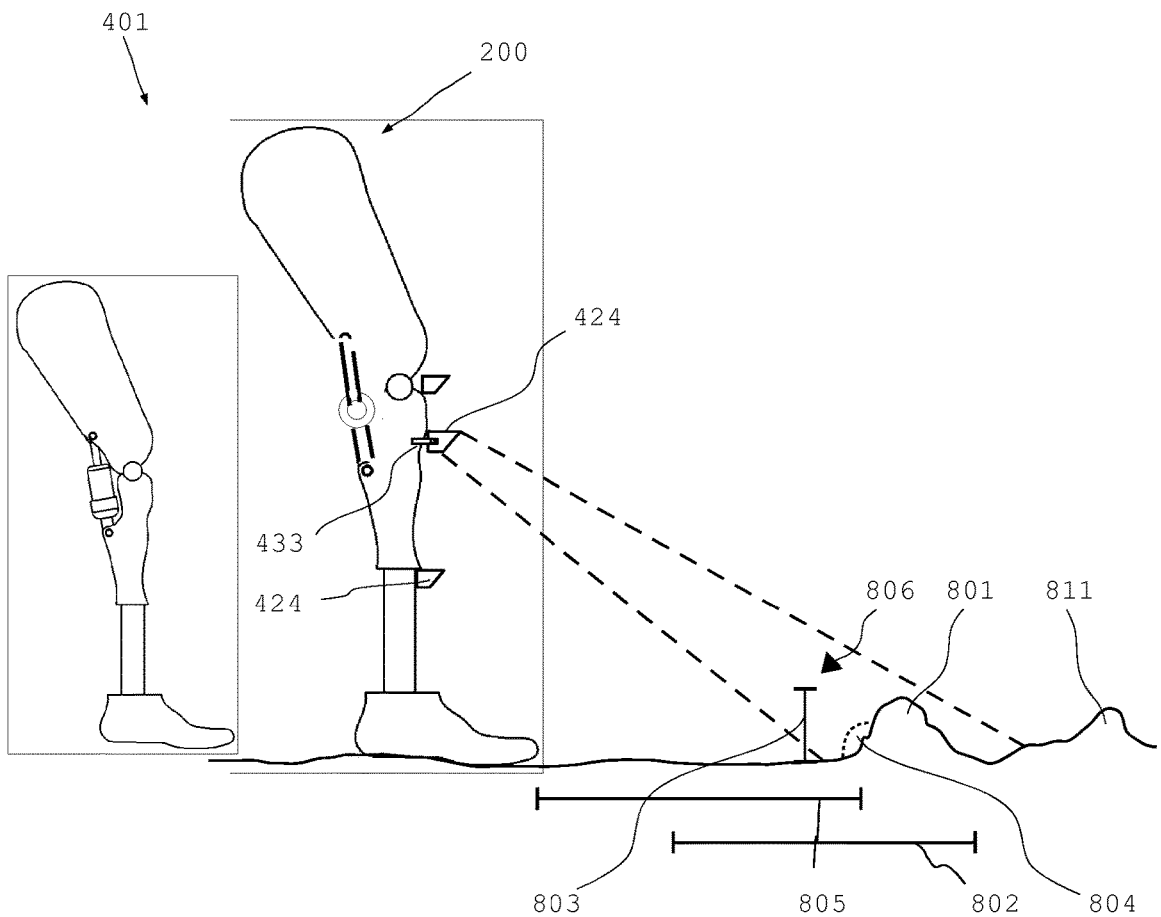
FIG. 2a shows a schematic view of the prosthesis according to FIG. 1 in a terrain.

FIG. 2a shows the prosthesis 200 of FIG. 1 in a very schematic terrain. In this case, areas of uneven ground 801, 811, which are sketched as elevations or unevennesses on the ground are situated along the path. By way of example, such areas of uneven ground can be: stones, steps, roots, depressions, bumps, potholes, ledges, elevations, curbs, cobblestones, tree stumps, branches and tree trunks.

Figure 3:
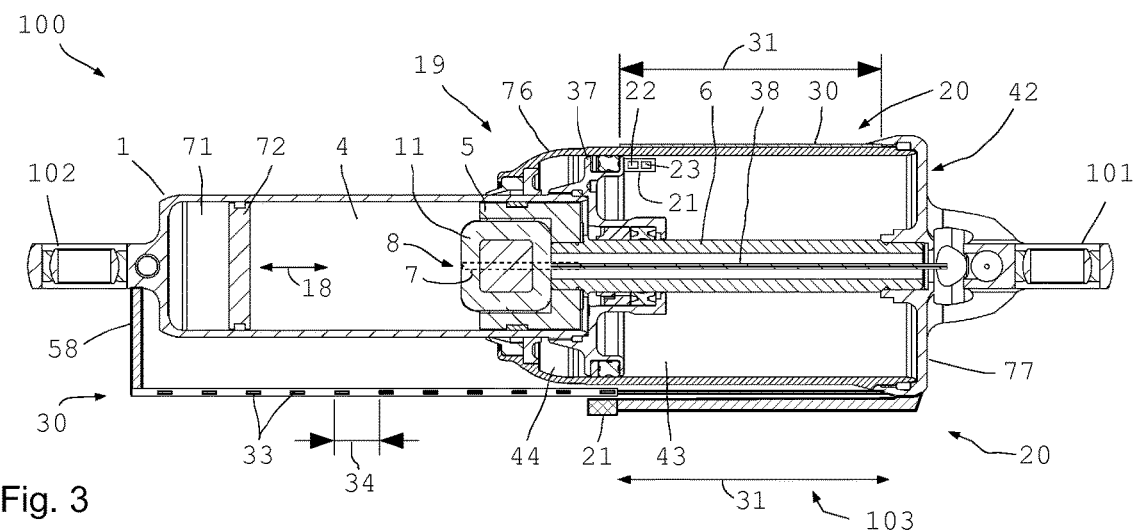
FIG. 3 shows a schematic view of a shock absorber device for the prosthesis according to FIG. 1.

Here, an ultrasound sensor 424 is attached by means of a holder device 433 to the prosthesis 200 illustrated in an enlarged manner. Here, the holder device 433 is dimensioned in such a way that it does not protrude, or only protrudes slightly, beyond the front of the body 111. As result, damage to the sensor unit 403 in the case of impact is largely avoided. In the prosthesis 200 that is illustrated in an enlarged manner, provision is made for a rotary damper which damps a rotary or pivot movement. The use of a linear damper, which is illustrated on the schematically illustrated smaller prosthesis in FIG. 3, is just as preferred.

The capture range 806 of the sensor 424 can be aligned in an ideal manner by pivoting the sensor 424 on the holder device 433. Preferably, such an alignment occurs once during the installation of the prosthesis or exoskeleton component 401. It is also possible here for the user themselves to undertake an alignment of the capture region 806 according to their desires.

The exemplary arrangements of the sensor unit 403 shown here serve illustrative purposes. In fact, it is preferable for only one sensor unit 403 to be provided at a prosthesis or an exoskeleton 200. However, the sensor unit 403 may comprise a plurality of sensors in this case. By way of example, four or six ultrasound sensors 424 may be provided in a sensor unit 403 such that the resolution can be improved or the capture region 806 can be expanded.

If use is made of a head up sensor 403, the latter, and hence the capture region 806, is pivoted in the direction in which the user looks or turns their head. However, a sensor unit 403 may also be provided on the control tube or on other parts that are not pivoted in the case of a head movement. The alignment of the sensor unit 403 with respect to the ground should be set depending on the type and design of the sensor in this case, or it should be ascertained in advance.

If the user wishes to use the identification device 408, he can activate the latter by the operating device 150. Then, the identification device 408 emits ultrasound waves into the capture region 806 by the sensor 424. If the section of terrain lying in the capture region 806 is free from areas of uneven ground, this is identified by the identification device 408 on the basis of the reflected ultrasound waves. Then, the identification device 408 does not undertake any adjustments of the damper setting. Here, the damper devices 1 are set as provided by the damper controller 300 during normal operation or as corresponds to the desired prescriptions of the user.

If an area of uneven ground 801 appears in the capture region 806 in due course, there is a modified reflection of the ultrasound waves. The change in signal is registered and evaluated by the identification device 408. On the basis of the identification, it is possible to determine, in particular, the height 803 of the area of uneven ground over the ground and the distance 805 of the area of uneven ground from the front side of the body or of the component 200. On the basis of the reflected signals, it is also possible to ascertain the angle 804 of an area of the area of uneven ground that points toward the prosthesis 200. It is also possible, for example, that the form or the three dimensional geometry of the area of uneven ground is characterized, at least approximately.

The identification device 803 ascertains the ideal time for adjusting the damper setting for the expected impact with the area of uneven ground 801 on the basis of the distance 805. Preferably, the damper setting remains unchanged until the area of uneven ground 801 is reached so that the best driving properties for a normal or plane ground are obtained. If the front point of the prosthesis now reaches the area of uneven ground 801, the identification device 408 actuates the central control device 60 in such a way that the damping is adjusted in the soft direction. Here, it is possible to use parameters such as the height 803 or the angle 804 in order to set the damper softer by precisely the measure that is ideal for such an area of uneven ground.

If the damper device 1 is adjusted by way of, for example, applying a field strength to a magnetorheological fluid 9, the damper adaptation may be effectuated immediately before striking the front wheel 111 on account of the particularly fast reaction time. The damper devices 1 with such short reaction times are particularly well-suited to the use with the identification device 408 since the capture region 806 can be focused to a near region 802 that is as short as possible. As a result, it is possible to avoid an unwanted identification of areas of uneven ground 801 which are no longer relevant at all after a spontaneous evasive movement.

The less far the near region 802 extends in front of the user, the more probable it is that the identified areas of uneven ground 801 become relevant and are not simply circumvented, for instance after changing direction. On account of the very short reaction time of the damper adjustment presented here, it is possible, for example, to realize near regions 802 which extend over a distance which the prosthesis or exoskeleton 200 traverses in one second or even in only one tenth of a second. Here, the adjustment time of the damper device 1 is preferably less than 10 milliseconds. Here, the near region 802, in which areas of uneven ground 801 are identified and able to trigger a damper adjustment, may be adapted dynamically by the identification device 408 depending on the respective walking or running speed.

Once the area of uneven ground 801 has been overcome and no further areas of uneven ground 811 are situated in the near region 802, the damper device 1 is restored back to the appropriate basic setting for flat terrain. By focusing the capture region 806 onto a very short near region 802, areas of uneven ground 811 lying outside of the near region 802 are not captured. However, this is by no means disadvantageous since frequent and fast changes of direction occur when walking or hiking in terrain. Therefore, it is not unlikely that areas of uneven ground 811 that are situated further away do not become at all relevant but are circumvented. The short near region 802 consequently is advantageous in that the damper device 1 is also adjusted precisely to the ground underfoot which is current at the moment.

A distinction between e.g. cobblestones and a gravel road (forest path) is very difficult by means of the detector signals according to the prior art (displacement signal; amplitude; acceleration signal) since the signals from the detector devices may be very similar on both grounds. However, the damper should have different settings to this end; this is possible using the identification of the surroundings:

A softer setting is expedient in the case of cobblestones so that shocks are not transmitted to the body. The risk of sudden elevations/holes is low; it follows from this that an unchanging characteristic is expected to be present over relatively long phases.

The damping is preferably set to be stiffer on a gravel path because the prosthesis can otherwise sink in too strongly and this may yield unstable states. Unstable states may result therefrom. Furthermore, the risk of sudden larger stones or areas of uneven ground is significantly larger on a forest path or on a gravel road, and so a quicker change of characteristics may also be necessary (higher clock rate of the electronics).

The identification device 408 shown here communicates with a detector device 20 of the damper device 1 (cf. FIG. 3). As described above, this detector device 20 is provided for ascertaining a relative speed of two components 101, 102 moving in relation to one another. On the basis of the relative speed captured by this detector device 20, the identification device 408 can independently monitor whether or not the undertaken damper adjustment was adequate for the overcome area of uneven ground 801.

By way of example, if the prosthesis or the prosthesis wearer 200 runs over an area of uneven ground 801 and there is a non-ideal load of the damper device 1 in the process, then this is identified by the identification device 408 on the basis of the inappropriate relative speed of the damper components 101, 102. Then, if a comparable area of uneven ground 801 occurs at a subsequent time, the monitoring device 408 undertakes the damper adjustment taking account of a suitable correction factor. If the relative speed of the damper components 101, 102 measured thereupon lies in the intended range, the identification device 408 keeps the correction factor. If the damper load is outside of the intended range again, the identification device 408 adapts the correction factor by a certain measure.

Here, the identification device 408 is equipped with a storage device 418 so that the properties of the identified area of uneven ground 801 and the thereupon undertaken damper adjustments and possible correction factors can be stored. Firstly, this facilitates particularly simple maintenance and control by the service, where the storage device 418 can be read out by way of a suitable interface.

However, moreover, it also provides the wearer with helpful information which they can retrieve, for example, by way of their smart phone 160 from the storage device 418. Particularly preferably, the information stored in the storage device 418 is linked to position data which can be added from, for example, a GPS-capable smartphone 160 or smart device (such as e.g. a smart watch). On the basis of this data, the user can create very detailed path profiles in conjunction with digital maps, said path profiles offering a very vivid image about the prevalent ground or terrain conditions on the basis of the stored areas of uneven ground.

It is also possible that the identification device 408 is embodied to identify a jump of the prosthesis wearer 200. By way of example, a jump can be captured by virtue of no, or only very little, reflection occurring or by virtue of a weight sensor in the shoe not capturing any weight. Such an identification of ground missing under the shoe of the user is advantageous in that the damper device 1 can be ideally set for the impact of the prosthesis wearer 200 after the jump. In order to identify whether the prosthesis wearer 200 lands first with the left leg or right leg after the jump, the identification device 408 may have at least one position sensor or the like.

In another configuration, the sensor unit 403 is preferably equipped with a reception unit 423 embodied as a camera. Using such a reception unit 423, optical projections of the area of uneven ground are captured and used for identifying areas of uneven ground by the identification device 408. Here, a transmission unit 413 is not required and may be omitted.

It is also possible for provision to be made of two or more reception units 423 embodied as cameras or at least one stereo camera such that optical projections with a three-dimensional or spatial information are derivable. As a result, it is possible to determine a distance, form and size of the area of uneven ground with particularly high detail and in a particularly reliable manner.

The sensor unit 403 may also comprise a camera with a light source and may be embodied as a triangulation device. Here, the light source projects a defined pattern onto the area of uneven ground and the camera records this pattern from a plurality of viewing angles and calculates the form or size of the area of uneven ground from the pattern distortion.

It is also possible that the sensor unit 403 emits light by means of a light source and the identification device 408 ascertains the distance to the area of uneven ground by means of a time-of-flight measurement.

FIG. 3 shows an exemplary embodiment of a shock absorber device 100 for a prosthesis or exoskeleton component 401 having a damper device 1 and, in this case, a spring device 42 which is embodied as an air spring and comprises a positive chamber 43 and a negative chamber 44. The damper device 1 is fastened to the first end as a connection unit or component 101 and the second end as connection unit or component 102 to different parts of the component 401 from FIG. 1 in order to damp relative movements. The damper device 1 comprises a damper housing 2 and a first damper chamber 3 and a second damper chamber 4, which are separated from one another by the damping valve 8 embodied as a piston 5. In other configurations, an external damper valve 8 is also possible, which is arranged outside of the damper housing 2 and connected by way of appropriate feed lines.

The piston 5 is connected to a piston rod 6. The magnetorheological damping valve 8 (indicated by dashed lines) is provided in the damping piston 5, said damping valve comprising here an electrical coil 11 as a field generating device, in order to produce a corresponding field strength. The damping valve 8 or the "open state" of the damping valve is actuated by means of the electrical coil device 11.

The coil of the electrical coil device 11 is not wound around the piston rod 6 in the circumferential direction but rather about an axis extending transversely with respect to the longitudinal extent of the piston rod 6 (and parallel to the plane of the drawing here). A relative movement takes place here linearly and occurs in the direction of movement 18.

The magnetic field lines run here in the central region of the core approximately perpendicularly with respect to the longitudinal extent of the piston rod 6 and therefore pass approximately perpendicularly through the damping ducts 7. A damping duct is located behind the plane of the drawing and is indicated by dashed lines. This brings about effective influencing of the magnetorheological fluid located in the damping ducts 7, with the result that the flow through the damping valve 8 can be damped effectively.

An equalization piston 72, which disconnects an equalization space 71, which is preferably filled with a gas, for the volume of the piston rod, which enters when spring compression occurs, is arranged in the damper housing 2.

Not only in the damping valve 8 but also here in the two damping chambers 3 and 4, there is a magnetorheological fluid present everywhere here (with the exception of the equalization space 71) as a field-sensitive medium.

The shock absorber device 100 has a detector device 20. The detector device 20 comprises in each case a detector head 21 and a scaling device 30 embodied in a structured fashion.

The scaling device 30 comprises here a sensor belt with permanent magnetic units as field generating units. The poles of the permanent magnetic units alternate with the result that north and south poles are arranged in alternating fashion in the direction of movement of the detector 22. The magnetic field strength is evaluated by means of the detector head, and the respective current position 19 is determined therefrom.

The spring device 42 extends here at least partially around the damper device 1 and comprises a spring housing 76. One end of the damper 1 is connected to a suspension piston 37 or forms the latter. The suspension piston 37 separates the positive chamber 43 from a negative chamber 44.

The spring housing 76 is closed off with respect to the end of the connecting unit 101 by a cover 77. The connecting cable 38 for the electrical coil device 11 is also led out there. An electrical connecting cable for the detector device 20 is also preferably led to the outside there.

For the sake of better clarification, two different variants of a detector device 20 are shown in FIG. 3.

The detector device 20 comprises two sensor parts, specifically the detector head 21, which, above the center line in the variant illustrated, is arranged inside the positive chamber 43 of the spring device 42. The detector device 20 comprises as a further sensor part the scaling device 30 which in this variant is arranged or held in the spring housing 76. Depending on the configuration and selection of material of the spring housing 76 and depending on the measuring principle of the detector device 20, the scaling device 30 can be integrated into the wall of the spring housing 76 or else arranged on the inner wall of the spring housing 76 or else attached on, or applied to, the spring housing 76 on the outside.

The detector head 21 comprises two detectors 22 and 23 which are arranged offset from one another in the direction of movement 18 in this case.

The scaling device 30 has a structure 32 which extends over a measuring section 31 and over which the physical properties of the scaling device 30 change periodically.

Sensor sections 33 are preferably arranged on the scaling device 30 and have electrical and/or magnetic properties which respectively repeat and therefore form the structure 32 of the scaling device 30.

If a relative movement of the connecting units 101 and 102 of the damper 1 with respect to one another now takes place, the position 19 of the damper 1 changes and the relative position of the detector head 21 relative to the scaling device 30 shifts. By evaluating the signal strength of a detector 22, 23 and, in particular, of at least two detectors 22, 23 it is therefore possible to infer the relative position of the detector head 21 relative to a sensor section 33 or with respect to the scaling device 30 or the absolute position within a sensor section 33. The sensor sections 33 have a length 34 which may be constant or else variable. If two detectors are arranged offset with respect to one another in the direction of movement 18 and if both detectors detect the magnetic field of the scaling device 30, the position 19 and the direction of movement 18 can be determined very precisely by evaluating the signals.

During the continuous movement, the number of sensor sections or periods passed is stored in the memory device 45 of the control device 46, with the result that the absolute position 19 can be inferred. All that is required for this is for the measuring frequency to be so high that a complete sensor section is not moved past "unnoticed" during a measuring cycle.

As an alternative to the variant plotted above the line of symmetry of the damper device 1 in FIG. 3, an alternative of the detector 20 is additionally illustrated below the line of symmetry, the detector device 20 being arranged completely outside of the damper housing 2 and outside of the spring housing 76 in this case. A holder 58 holds the scaling device 30 and connects the scaling device securely to an end or a connection unit 102 of the shock absorber device 100. The detector head 21 is connected to the other end or the other connection unit 101 of the shock absorber device 100. The detector head 21 is held in such a way that it is arranged without contact at a small distance from the scaling device 30. In the case of a relative movement between the connection units of the shock absorber 100, there thus also is a relative movement of the scaling device 30 relative to the detector head 21. Here too, a relative position can be ascertained by way of the measuring section 31, which preferably substantially corresponds to the damper stroke 103, by way of evaluating the field strengths.

LIST OF REFERENCE SIGNS

1 Damper device
2 Damper housing
3 First damper chamber
4 Second damper chamber
5 Damping piston
6 Piston rod
7 Damping duct
8 Damping valve
9 MRF
10 Damper characteristic
11 Electrical coil
12 Control circuit
18 Direction of movement
19 Position
20 Detector device
21,22 Detector
30 Scaling device
31 Measuring section
32 Structure
33 Sensor section
37 Suspension piston
38 Cable
42 Spring device
43 Positive chamber
44 Negative chamber
42 Insulation material
45 Storage device
46 Control device
48 Data
49 Display
52 Step
53 Internet
54 Network interface
55 Radio network interface
56 Step
57 Touchscreen
58 Holder
60 Control device
61 Battery unit
70 Step
71 Equalization space
72 Equalization piston
76 Spring housing
77 Cover
90 Damper characteristic
100 Shock absorber
101,102 Component
118 Angle sensor
150 Operating device
151 Actuating device
152 Adjustment device
153 Input unit
160 Smartphone
161-162 Region
190 Damper characteristic
200 Prosthesis, exoskeleton
401 Prosthesis or exoskeleton component
403 Sensor unit
408 Identification device
413 Transmission unit
418 Storage device
423 Reception unit
424 Ultrasound sensor
433 Holding device
434 Infrared sensor
444 Radar sensor
476 Sensor module
801 Area of uneven ground
802 Near region
803 Height
804 Angle
805 Distance
806 Capture region
811 Area of uneven ground

The invention claimed is:

1. A component for a prosthesis or an exoskeleton, the component comprising:
a shock absorber device with a damper device that is controllable by way of a control device;
an identification device with a sensor that includes a receiver for contactless acquisition of a signal influenced by an area of uneven ground and related to an area in front of said sensor in a direction of movement of the prosthesis or exoskeleton;
wherein said identification device is configured to identify the area of uneven ground in dependence on the signal captured by said receiver and to control said damper device in dependence on the identified area of uneven ground so that a damping property of said damper device is adjusted by a signal of said identification device before the prosthesis or exoskeleton reaches the area of uneven ground.

2. The component according to claim 1, wherein said sensor comprises a transmission unit for emitting a signal and wherein said reception unit is configured to capture at least one reflection of the emitted signal, originating from the area of uneven ground, as a signal.

3. The component according to claim 1, wherein said damper device comprises at least one first damper chamber, at least one second damper chamber, and at least one controllable damping valve coupling said first and second damper chambers to one another, and wherein a field generating device that is controllable by said identification device is assigned to said damping valve, said field generating device serving to generate and control a field strength in at least one damping duct of said damping valve, wherein a field-sensitive rheological medium is provided in the damping duct.

4. The component according to claim 1, wherein said identification device is configured to only take account of areas of uneven ground in a predetermined near region for controlling said damper device.

5. The component according to claim 4, wherein said identification device is configured to predetermine the near region depending on a walking speed of the prosthesis and wherein the near region extends over a distance which the prosthesis wearer covers in one second on a basis of a walking speed.

6. The component according to claim 1, wherein said identification device is configured to adjust the damping property of said damper device in less than 30 milliseconds as a consequence of an identified area of uneven ground in the near region.

7. The component according to claim 1, wherein said identification device is configured to ascertain a height of the area of uneven ground over the ground and/or an angle of at least one region of the area of uneven ground with respect to the ground and to take account of the height and/or the angle for controlling said damper device.

8. The component according to claim 1, wherein said control device is configured to adjust the damping property of said damper device to be stiffer until the area of uneven ground is reached.

9. The component according to claim 1, wherein said identification device is configured to take account of at least one preset threshold for a maximum and/or a minimum damping when controlling said damper device.

10. The component according to claim 1, wherein at least one sensor module for capturing a damper load is assigned to said damper device and wherein said identification device is configured to read said sensor module and register the damper load as a consequence of an adjustment of the damper property carried out in response to an identified area of uneven ground and to adapt a control of said damper device in a case of a deviation of the registered damper load from a predetermined measure for the damper load.

11. The component according to claim 1, wherein said identification device comprises at least one storage device for recording identified areas of uneven ground.

12. The component according to claim 1, wherein said sensor is arranged on a pivotally supported head.

13. The component according to claim 1, wherein said sensor is pivotally mounted on a holder device, enabling a transmission angle and/or reception angle in relation to the ground to be adjustable.

14. The component according to claim 1, wherein said sensor is at least one sensor device selected from the group consisting of an ultrasound sensor, an infrared sensor, and a radar sensor.

15. The component according to claim 1, wherein said identification device is configured to control at least two said shock absorber devices.

16. A method for operating a prosthesis or exoskeleton component of a prosthesis or of an exoskeleton, the component having at least one shock absorber device with a damper device that is controlled by way of a control device, the method comprising:
  contactlessly capturing at least one signal with an identification device and identifying an area of uneven ground in front of the prosthesis or exoskeleton in a direction of movement thereof on a basis of the contactlessly captured signal; and
  controlling the damper device in dependence on the identified area of uneven ground and adjusting a damping property of the damper device on a basis of the identified area of uneven ground before the prosthesis or exoskeleton reaches the area of uneven ground.

17. The method according to claim 16, which comprises emitting at least one signal with the identification device, receiving a reflection of the emitted signal originating from the area of uneven ground, and capturing the reflection as the at least one signal.

18. The method according to claim 16, which comprises adjusting the damper device to be stiffer after identifying the area of uneven ground until the area of uneven ground is reached.

* * * * *